(12) United States Patent
Zhao et al.

(10) Patent No.: US 11,630,041 B2
(45) Date of Patent: Apr. 18, 2023

(54) METHOD FOR OBTAINING ROCK MECHANICAL-GEOMETRIC PARAMETERS AND HOLOGRAPHIC SCANNING SYSTEM

(71) Applicant: Tianjin University, Tianjin (CN)

(72) Inventors: Gaofeng Zhao, Tianjin (CN); Yiming Li, Tianjin (CN)

(73) Assignee: Tianjin University, Tianjin (CN)

(*) Notice: Subject to any disclaimer, the term of this patent is extended or adjusted under 35 U.S.C. 154(b) by 205 days.

(21) Appl. No.: 17/149,745

(22) Filed: Jan. 15, 2021

(65) Prior Publication Data
US 2021/0223153 A1    Jul. 22, 2021

(30) Foreign Application Priority Data
Jan. 17, 2020  (CN) .......................... 202010053143.4

(51) Int. Cl.
| | |
|---|---|
| *G01N 3/46* | (2006.01) |
| *G01N 1/32* | (2006.01) |
| *G01N 1/28* | (2006.01) |
| *G02B 26/10* | (2006.01) |
| *G01N 3/08* | (2006.01) |

(52) U.S. Cl.
CPC .............. *G01N 3/46* (2013.01); *G01N 1/286* (2013.01); *G01N 1/32* (2013.01); *G01N 3/08* (2013.01); *G02B 26/106* (2013.01); *G01N 2001/2866* (2013.01)

(58) Field of Classification Search
CPC ............ G01N 3/46; G01N 3/08; G01N 1/286; G01N 1/32; G01N 2001/2866; G02B 26/106

USPC ............................................................. 73/81
See application file for complete search history.

(56) References Cited

U.S. PATENT DOCUMENTS

| | | | |
|---|---|---|---|
| 6,349,595 B1* | 2/2002 | Civolani .................. | G01N 3/42 73/152.02 |
| 2015/0068292 A1* | 3/2015 | Su ............................ | G01N 3/46 73/82 |
| 2017/0370193 A1* | 12/2017 | Glover .................. | E21B 49/005 |

* cited by examiner

*Primary Examiner* — Nathaniel T Woodward
(74) *Attorney, Agent, or Firm* — JCIP Global Inc.

(57) ABSTRACT

The invention discloses a method for obtaining the geometrical and mechanical parameters of rock samples and a holographic scanning system thereof, wherein the system includes an observation mechanism, a multi-scale penetration mechanism, a grinding mechanism, a rock sample installation mechanism arranged on a three-axis precision motion platform, and an industrial computer controlling the operation mode of each mechanism of the platform Indentation/rotary penetration test, pulse echo signal acquisition, three-dimensional surface topography reconstruction, layer by layer grinding and repeated experiments are carried out. The geometric parameters and corresponding mechanical field parameters are obtained by spatial interpolation of the three-dimensional parameter lattice accumulated by several layers of single-layer rock parameters. The holographic scanning system and method can obtain the real spatial distribution of various media in rock samples. Combined with high performance numerical calculation method, it provides a more scientific method for the analysis of rock mechanical properties, failure and instability.

8 Claims, 4 Drawing Sheets

METHOD FOR OBTAINING ROCK MECHANICAL-GEOMETRIC PARAMETERS AND HOLOGRAPHIC SCANNING SYSTEM

CROSS-REFERENCE TO RELATED APPLICATION

This application claims the priority benefit of China application serial no. 202010053143.4, filed on Jan. 17, 2020. The entirety of the above-mentioned patent application is hereby incorporated by reference herein and made a part of this specification.

BACKGROUND

Technical Field

The invention covers the technical field of rock parameter measurement, especially for obtaining rock geometric-mechanical parameters and a holographic scanning system.

Description of Related Art

The acquisition of rock material parameters is the basic of the underground engineering, and it is the common goals for researchers to obtain the mechanical parameters of rock accurately and quickly. Due to the diversity and complexity of the internal structure of rock materials, the mechanical parameters in meso-scale can't be accurately quantified in theory and numerical simulation. Therefore, the numerical results often varied from actual observation, and the rock engineering went far beyond the current theory of rock mechanics. With the development of measurement and analysis technology, many researchers began to investigate the internal structure and the spatial distribution of rock materials in meso-scale. Numerous studies have shown that due to the heterogeneous internal medium of rock samples in meso-scale, it shows nonlinearity of macroscopic mechanical behavior in rock fracture process. Moreover, it is hard to input the accurate microscopic parameters in the numerical model, and most of which are qualitatively assigned parameters by introducing statistical models. Digital image technology can better reflect the different medium of the meso-structure of geotechnical material though gray scale value or color distribution to classify mesoscopic medium and determine the actual geometric distribution of rock materials.

The most commonly used technology for obtaining three-dimensional geometric parameters of rock materials is the X-ray CT scanning technology, which takes advantage of the strong penetration of X-rays, and the three-dimensional geometric parameters of the rock materials are quickly obtained by scanning the rock samples layer by layer with micro-focus X-ray without damaging the internal structures of rock. However, the disadvantage is that the image obtained by CT scanning is essentially the distribution of X-ray wave velocity. When the density contrast between the adjacent different medium is weak in rock materials, there is no clear image through the X-ray. Moreover, the X-ray CT scanning technology can't obtain the mechanical parameters.

At present, there are various approaches to obtain rock mechanical parameters rapidly. For example, the professor Li from Xi'an University of Technology proposed the rotary cutting penetration test to acquire rock mechanical parameters (such as compressive strength, cohesive, friction angle) according to the dynamic equilibrium relationship between rotary cutting bit and rock. In addition, the penetration test is a recommended test of the International Society of Rock Forces (ISRM) for obtaining rock mechanical parameters. This kind of test is more efficient but low accuracy. The main reason is that the boundary conditions of the experiment are complex. If could combine with numerical simulation in dealing with complicated boundary conditions, the mechanical parameters of rock materials can be obtained rapidly and accurately. In this invention, the aim is to construct an automated device to obtain the rock mechanical and geometric parameters field in three dimension combining the principle of CT scanning, penetration test, binocular stereo vision, and 3D printing.

SUMMARY

The purpose of this invention is to obtaining rock mechanical and geometric parameters field in three dimension, and design an automated device to obtain the rock parameters rapidly and accurately.

The technical scheme of the invention is as follows:

A method for obtaining rock mechanical and geometric parameters, the steps are as follows:

S1. Acquiring a clear images of rock surface by utilizing high accuracy CCD fixed-focus camera in the observation cabin;

S2. Dividing the upper surface of the rock sample into N1×N1 grids with high resolution (on a micro scale) by laser, and then using the Berkovich indenter for indentation test in each grid according to the preset loading rate $w_1$ and indentation depth $L_1$, so as to obtain the dynamic signal of displacement changing with time $D_1(t)$ by the displacement measurement system during each indentation process and the dynamic signal of load changing with time $F_1(t)$ by the pressure sensor which is sitting at the bottom of the rock sample, and then obtaining three-dimensional mechanical parameter lattice of the corresponding rock sample including elastic modulus E and Poisson's ratio $\mu_i$ by processing the above parameters;

And/or, dividing the upper surface of the same rock sample into $N_2 \times N_2$ grids with low resolution (on a macro scale) by laser, and then using the twist drill for rotary cutting penetration test in each grid according to a preset drilling rate $w_2$ and drilling depth $L_2$, so as to obtain the dynamic signal of feed force changing with time P(t) by the feed force sensor connected with the twist drill during each cutting process, the dynamic signal of torque changing with time M(t) by the torque sensor set at the adjacent side of the twist drill during each cutting process, and the dynamic signal of displacement changing with time $D_2(t)$ by the displacement measurement system during each cutting process, and then obtaining the three-dimensional mechanical parameters including elastic modulus E, cohesive force C and internal friction angle co and compressive strength $R_p$;

S3. Acquiring a pulse echo signal of the rock sample by the ultrasonic sensor excitation device and ultrasonic sensor receiving device which are symmetrically arranged on both sides of the rock sample, so as to obtain the longitudinal wave velocity $V_p$ and transverse wave velocity $V_s$ of the ultrasonic wave passing through the rock sample and the density ρ of the rock sample, and then calculating the dynamic elastic modulus Ed and dynamic Poisson's ratio $\mu_d$ of the rock sample;

$$E_d = \frac{\rho V_s^2(3V_p^2 - 4V_s^2)}{V_p^2 - V_s^2}, \quad \mu_d = \frac{V_p^2 - 2V_s^2}{2(V_p^2 - V_s^2)};$$

S4. Moving the rock sample to the same position as step S1 again, and then projecting the structured light coding pattern on the upper surface of the rock sample, so as to collect images of the upper surface of the rock sample by two cameras which are symmetrically and obliquely arranged above the rock sample, and reconstruct the three-dimensional morphology of the upper surface of the rock sample further;

S5. Polishing the surface of the rock sample, and lubricating and cooling by running water until the upper surface of the rock sample returning to a smooth plane;

S6. Repeating steps S1~S5 to grind the rock sample layer by layer and carrying out the same parameter acquisition experiment until the rock sample reaches the last layer of the preset depth, so as to acquire the 3D parameter lattice of the complete rock sample geometry and mechanics from the accumulation of several layers of single-layer rock parameters;

S7. Using IDW spatial interpolation algorithm to process the three-dimensional lattice of mechanical parameters obtained from step S6:

$$R(x) = \sum_{i=0}^{n} \frac{\omega_i(x) u_i}{S},$$

Wherein, $$\omega_i(x) = \frac{1}{\ln(d(x, x_i))}; \quad S = \sum_{j=0}^{N} \omega_j(x);$$

$x_i$ is the ith sample point; x is the unsolved point; $\omega_i(x)$ is the weight of $x_i$; $u_i$ is the value of $i^{th}$ actual sample point; R(x) is the mechanical parameters of rock obtained from different mechanical tests (indentation test, rotary cutting penetration test); $d(x,x_i)$ is the distance between the measured point and unsolved point:

$$d(x,x_i) = \sqrt{(x-x_i)^2 + (y-y_i)^2 + (z-z_i)^2},$$

Wherein, $x_i$, $y_i$, $z_1$ are the coordinates of the ith sample point on the X, Y, and Z axes, respectively;

Obtaining a virtual lattice of mechanical parameters by weighted averages using distances between interpolation points and the sample points as weight, and then obtaining the three-dimensional mechanical parameter fields of the whole rock sample, including compressive strength field, cohesive force field, internal friction angle field, elastic modulus field and Poisson's ratio field.

Further, when indentation test is conducted, the value of $N_1$ varies according to the shape of indenters, and ranges from 50×50 to 100×100, and the area of Berkovich indenter is 1/200~1/50 of the upper surface area of rock sample, and the preset depth is from 0.5 mm to 2 mm with quasi-static loading.

Further, when indentation test is conducted, the specific method to obtain the three-dimensional mechanical parameters is as follows:

Correlating the elastic modulus of rock sample and indenter by the reduction of elastic modulus $E_r$, and the formula for calculating indentation hardness $H_I$ from indentation test is:

$$H_I = \frac{P_{max}}{A_c},$$

Wherein, the formula of reduction of elastic modulus $E_r$ is:

$$E_r = \frac{\sqrt{\pi}}{2} \frac{S}{\sqrt{A_C}},$$

Wherein, the formula of elastic modulus $E_i$ is:

$$E_i = (1 - v_i^2)\left(\frac{1}{E_r} - \frac{1-v_s^2}{E_s}\right)^{-1},$$

Wherein, $P_{max}$ is the maximum indentation force; $E_s$ is the elastic modulus of indenter; $v_s$ is the Poisson's ratio of indenter; $u_i$ is the Poisson's ratio of rock sample;

Wherein, $A_c$ is the projected area of indenter:

$A_C = 24.5 h_C^2,$

Wherein, $h_c$ is the pressure depth, which is obtained by the following formula:

$$h_C = L - \frac{3P_{max}}{4S},$$

Wherein, S is the unloading stiffness, which is obtained from the load-displacement curves at the unloading stage, and the tangent slope at one third of the curve is taken as the unloading stiffness.

Further, when rotary cutting penetration test is conducted, the details of how to obtain three-dimensional mechanical parameters of rock samples are as follows:

Assuming the feed displacement per revolution is proportionate to the bit pressure P and torque M, $$\frac{1}{K_p} = \frac{1}{2}\tau_f R \delta_c \tan\left(\frac{\pi}{2} - \beta\right),$$

$$\frac{1}{K_m} = \frac{1}{2}\tau_f R^2 \delta_c^2,$$

Wherein, $K_p$ is the slope of the feed displacement-bit pressure curve, which is obtained from signals P(t) and $D_2(t)$; $K_m$ is the slope of the feed displacement-bit torque curve, which is obtained from M(t) and $D_2(t)$; $\beta$ is the mean friction angle of the bit; $\tau_f$ is the tensile strength of rock sample; R is radius of the bit, and the cutting coefficient is:

$$\delta_c = \frac{\cos \beta}{\sin \phi \cdot \cos(\phi + \beta)},$$

Wherein, the mean friction angle of the bit $\beta$ is:

$$\beta = \frac{\pi}{2} - \arctan\frac{RK_m}{K_p},$$

Wherein, cutting angle is:

$$\phi = 45° - \frac{\beta}{2},$$

Wherein, the friction angle φ is:

φ=90°−2ϕ,

Wherein, the normal stress σ and tangential stress τ is obtained from:

$$\sigma = \frac{P}{2aR\sec\theta\tan\phi},$$

$$\tau = \frac{P}{2aR\sec\theta},$$

Wherein, θ is the bit angle. According to the Mohr-coulomb criterion, the cohesive of rock sample is obtained as follows:

$$C = \tau - \sigma\tan\varphi = \frac{P}{2aR\sec\theta} - \frac{P}{2aR\sec\theta\tan\phi},$$

Wherein, the compressive strength of rock sample is:

$$R_p = \frac{2C\cos\varphi}{1-\sin\varphi},$$

Wherein, according to the energy conservation theory, the total work done by bit is mainly used to convert into internal energy $W_{inter}$, work done by rock cutting $W_{切}$, and work done by pressing into rock sample $W_{压}$, and the corresponding formula is:

$$W_{total}=W_{inter}+W_{cutting}+W_{press},$$

Wherein, according to the bit pressure-time curve $P_{(t)}$, the drilling speed v, the bit torque-time curve $M_{(t)}$, and rotation speed of bit ω, the internal energy $W_{inter}$ is:

$$W_{total} = \int_t P_{(t)} \cdot v \cdot dt + \int_t M_{(t)} \cdot \omega \cdot dt,$$

Wherein, the drilling speed is obtained from:

$$V = \frac{L}{t},$$

Wherein, L is the predetermined depth, t is the drilling time;

Wherein, the internal energy $W_{inter}$ is obtained from:

$$W_{inter} = \int\int\int_{\Omega 1} T_1(\Delta T)C_1 dv + \int\int\int_{\Omega 2} T_2(\Delta T)C_2 dv,$$

Wherein, $T_1(\Delta T)$ is the temperature distribution function of drill; $T_2(\Delta T)$ is the temperature distribution function of rock samples; $C_1$ is the specific heat of drill; $C_1$ is the specific heat of rock samples; $\Omega_1$ is the domain size of drill; $\Omega_2$ is the domain size of rock samples; $T_1(\Delta T)$ is the temperature difference of drill before and after drilling; $T_2(\Delta T)$ is the temperature difference of rock samples before and after drilling;

Wherein, the work done by cutting rock samples can be divided into two parts: the work done by the crushing torque, and the work done by friction torque:

$$W_{Cutting}=\int M_{Crush}\cdot\omega dt+\int M_{Friction}\cdot\omega dt,$$

and elastic modulus of rock samples E is obtained from:

$$E = \frac{F_2^2 L}{2\pi R^2 C(W_{total} - W_{inter} - W_{cutting})}.$$

Further, when indentation test is conducted, the value of $N_2$ varies according to the shape of drill bits, and ranges from 10×10 to 50×50, and the diameter of drill is 1/50 to 1/10 of the upper surface area of rock sample, and the preset depth L2 is from 0.5 mm to 2 mm.

Further, in step S3, the wavelength emitted by the ultrasonic sensor excitation device is one tenth of the path length through the rock sample.

A holographic scanning system for realizing the method for obtaining the geometrical and mechanical parameters of rock samples, wherein the equipment includes a observation mechanism 4 arranged on a three-axis precision motion platform 7, a multi-scale penetration mechanism 3, a grinding mechanism 2, a rock sample installation mechanism, and an industrial computer for controlling the operation of three-axis precision motion platform 7, the observation mechanism 4, the multi-scale penetration mechanism 3, the grinding mechanism 2 and the rock sample installation mechanism; wherein, The three-axis precision motion platform 7 comprises a first motion mechanism which could realize up and down motion, a second motion mechanism which is arranged on the first motion mechanism and could realize left and right motion, a third motion mechanism which is arranged on the second motion mechanism and could realize back and forth motion, and a cover plate which is located above the three motion mechanisms; wherein the observation mechanism 4, multi-scale penetration mechanism 3, and grinding mechanism 2 are successively installed on the floor of the cover plate, and the rock sample installation mechanism is installed on the third moving mechanism;

The observation mechanism 4 comprises a micro projector 19 arranged on the bottom surface of the cover plate and a first camera 17, and a second camera 18 symmetrically arranged on both sides of the micro projector 19; wherein the lens of the first camera 17 and the lens of the second camera 18 are arranged in an oblique manner towards the micro projector 19;

The multi-scale penetration mechanism 3 comprises a rotary cutting penetration device at the front side, an indentation detection device at the rear side, and a displacement measurement system arranged between the rotary cutting penetration device and the indentation detection device; wherein, the rotary cutting penetration device comprises a first rigid servo motor, a first ball screw, a feed force sensor and a standard twist drill which are connected from top to bottom in turn, and a displacement measurement system arranged between the rotary cutting penetration device and the indentation detection device. The indentation detection device includes a second rigid servo motor, a second ball screw, a vertical rigid spindle and a triangular shell type indenter connected from top to bottom in turn;

The rock sample installation mechanism comprises a square steel fixture 10 for fixing the rock sample 8, an ultrasonic sensor exciting device 9 and an ultrasonic sensor receiving device 11 symmetrically arranged on both sides of the square steel fixture; a pressure sensor for detecting the pressure on the rock sample is also arranged on the third moving mechanism of the square steel fixture 10.

Further, the grinding mechanism 2 comprises a grinding wheel and a drying device; wherein the drying device is an annular disc-shaped structure sheathed on the outer side of the grinding wheel, on which a plurality of hot air pipes are arranged along the annular direction, and each hot air pipe is connected with the hot air circulation box through a pipeline, so that the hot air is vertically ejected from the top surface of the rock sample 8 through a plurality of hot air pipes.

Compared with the existing technology, the highlights of rock mechanical and geometric parameters and holographic scanning system are as follows:

(1) the holographic scanning system integrates digital camera, multi-scale rotary cutting penetration device and automatic grinding machine through three-way movable operation platform, effectively improves the use efficiency of three kinds of instruments, and has a higher degree of automation and intelligence;

(2) the holographic scanning system uses a grinding cycle system to grind the rock samples layer by layer, and take a quick photo of each layer of rock surface. Through digital image processing, the real three-dimensional microstructure of rock samples can be obtained. Compared with the traditional CT scanning technology, the accuracy of the three-dimensional microstructure image is higher, and the three-dimensional geometric parameters obtained by CT scanning technology are calibrated and verified;

(3) the holographic scanning system adopts the multi-scale rotary cutting penetration technology, which can obtain the real three-dimensional micro geometric parameters of rock, and at the same time, through the multi-scale dynamic penetration of each layer of rock, the three-dimensional mechanical parameter field of each layer of rock sample at different scales can be obtained;

(4) the holographic scanning system adopts the binocular stereo vision imaging technology based on structured light, scans the target rock surface which has been indented (cut) through the three-dimensional vision system, and obtains the three-dimensional morphology of the indentation (groove), so as to evaluate the dynamic crushing efficiency of the multi-scale cutting device;

(5) the holographic scanning system uses digital image measurement technology and three-dimensional interpolation calculation method to reconstruct the geometric parameters and mechanical parameters of rock samples, which can obtain the real spatial distribution and corresponding mechanical parameter field of various media in rock samples. Combined with high performance numerical calculation method, it can provide a more scientific method for the analysis of rock mechanical properties, failure and instability.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

The method for obtaining rock mechanical and geometric parameters of the present invention will be described in detail below with reference to the embodiments and the accompanying drawings.

Embodiment 1

Figure 1:
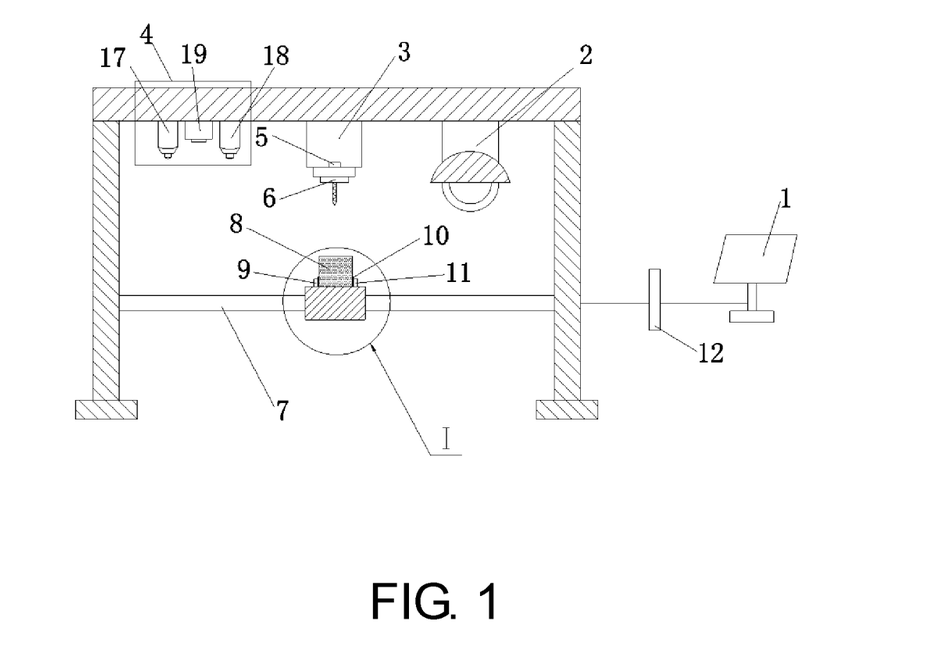
FIG. 1 is a schematic of rock mechanical-geometric parameters and holographic scanning system.
Figure 2:
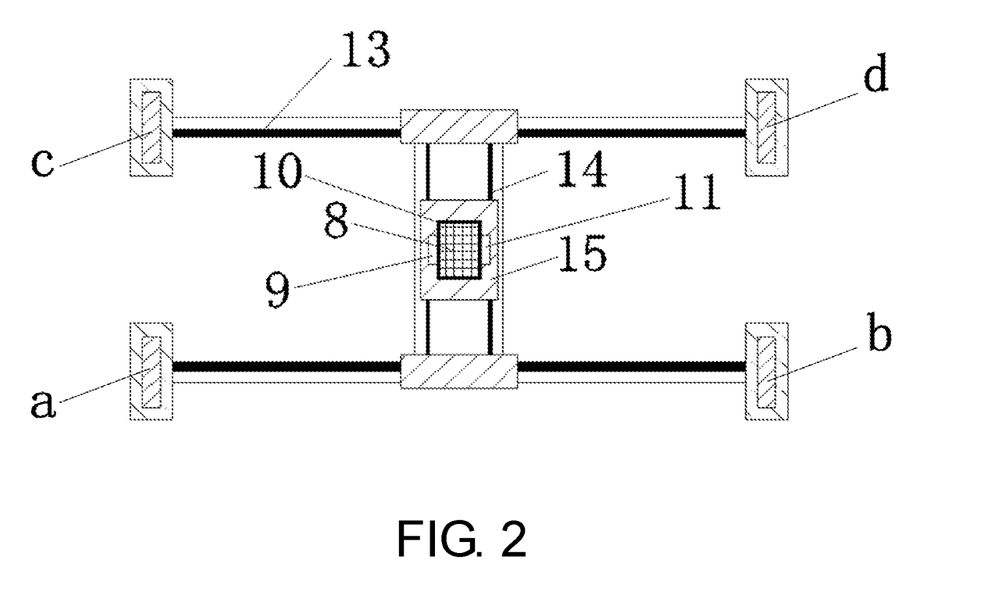
FIG. 2. is a main view of the three-axis precision motion platform in rock mechanical-geometric parameters and holographic scanning system.
Figure 3:
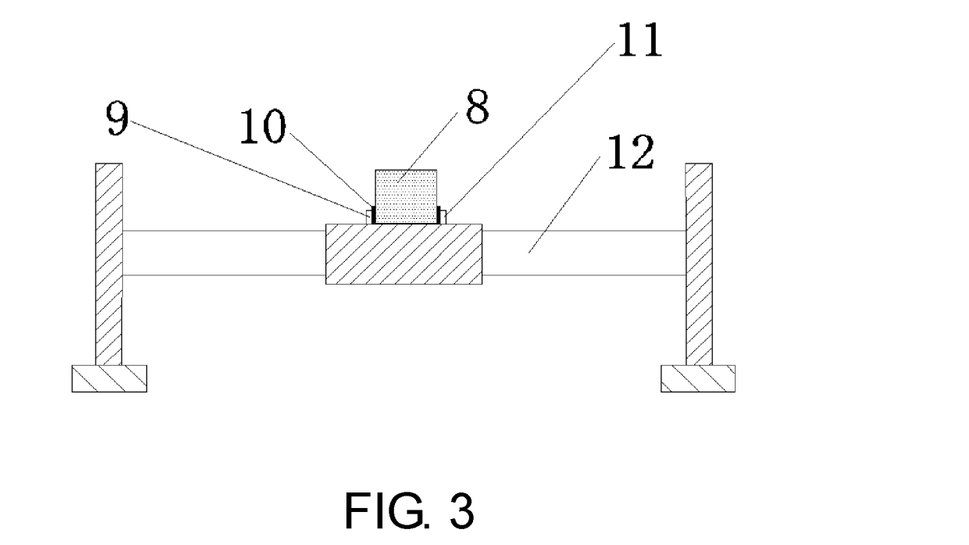
FIG. 3. is a top view of the three-axis precision motion platform in rock mechanical-geometric parameters and holographic scanning system.
Figure 4:
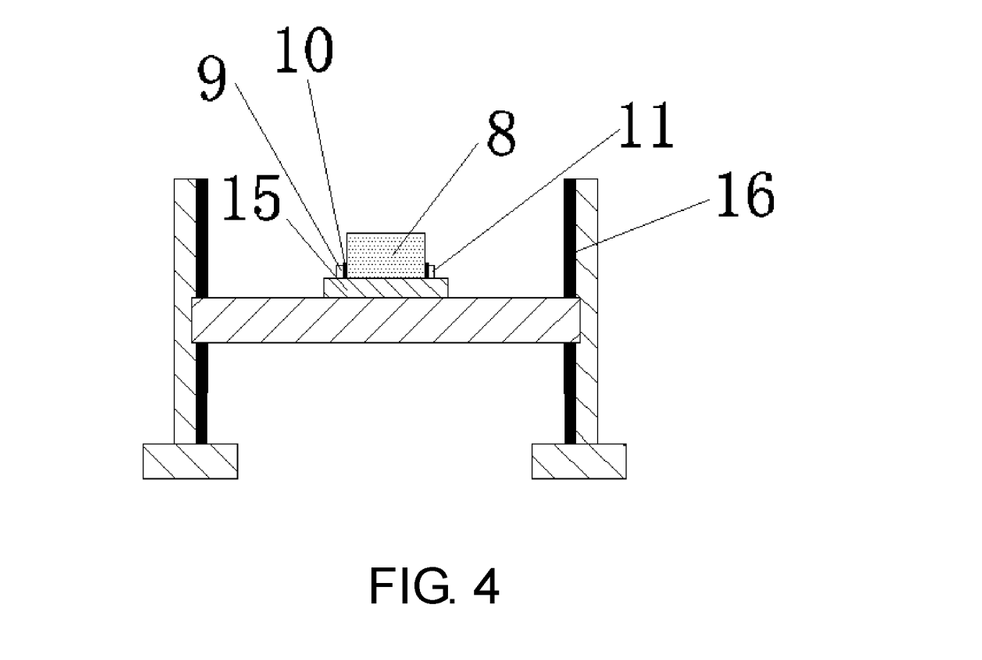
FIG. 4. is a left view of the three-axis precision motion platform in rock mechanical-geometric parameters and holographic scanning system.
Figure 5:
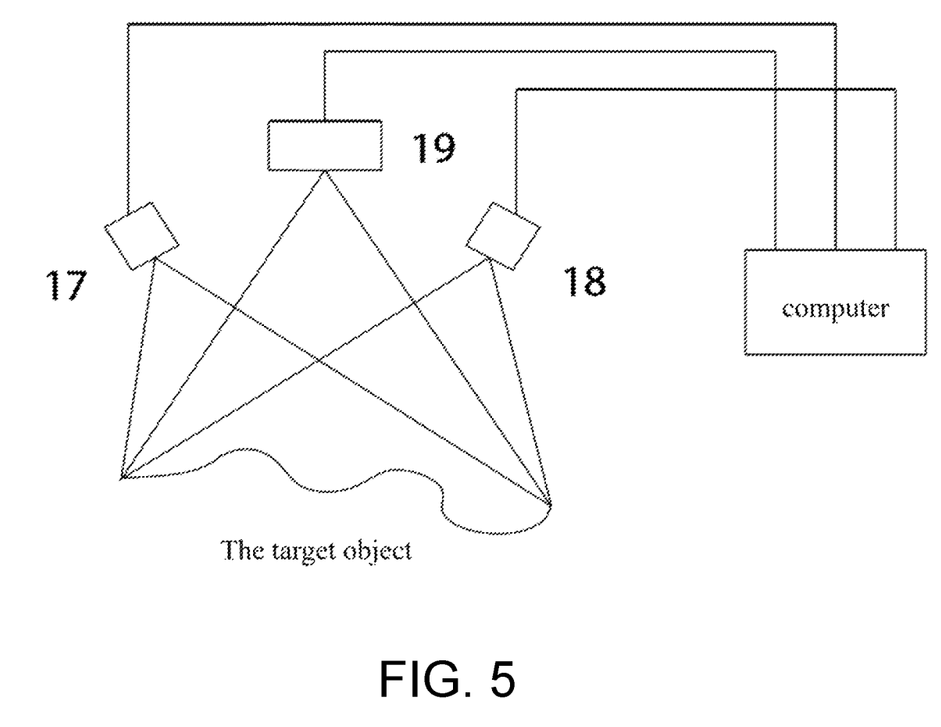
FIG. 5. is a schematic of observation mechanism in rock mechanical-geometric parameters and holographic scanning system.

As shown in FIG. 1, a holographic scanning system, which includes a observation mechanism 4 arranged on a three-axis precision motion platform 7, a multi-scale penetration mechanism 3, a grinding mechanism 2, a rock sample installation mechanism, and an industrial computer for controlling the operation of three-axis precision motion platform 7, the observation mechanism 4, the multi-scale penetration mechanism 3, the grinding mechanism 2 and the rock sample installation mechanism; wherein, As shown in FIG. 2, the three-axis precision motion platform 7 is purchased from common commercially available equipment, which includes the first support column a, the second support column B, the third support column C and the fourth support column D. between the first support column A and the second support column B, and between the third support column C and the fourth support column D, there is a horizontal longitudinal rail 13 on each of the two horizontal rails, Each longitudinal rail 13 is provided with a first sliding block which can move back and forth on the longitudinal rail, at the same time, a vertical rail 16 is respectively arranged on the side wall of each supporting column which is in contact with the horizontal longitudinal beam, and the two ends of each horizontal longitudinal beam are respectively provided with a second sliding block which is matched with the vertical rail, so that the horizontal longitudinal beam can move back and forth along the vertical rail 16 in the axial direction The sliding block is fixed with a first bearing platform 15, on which two transverse rails 14 are symmetrically erected along the direction perpendicular to the horizontal longitudinal beam, each transverse rail 14 is provided with a third sliding block matched with it, and the second bearing platform 15 is fixed on the two third sliding blocks, so that the second bearing platform 15 can use the third sliding block to slide back and forth along the two transverse rails 14; on each supporting column, each horizontal rail 14 is fixed with a second bearing platform 15 The longitudinal beam, the first bearing platform 15 and the second bearing platform 15 are also provided with a plurality of servo motors for controlling the movement of two first sliding blocks, four second sliding blocks and two third sliding blocks respectively, and each servo motor is connected with the corresponding sliding blocks through a ball screw to control the movement of the sliding blocks;

As shown in FIG. 1, a horizontal cover plate is fixed on the top surface of the first support column a, the second support column B, the third support column C and the fourth support column D, so that the observation mechanism, the multi-scale penetration mechanism and the grinding mechanism are arranged on the bottom surface of the cover plate in turn along the axial direction of the horizontal longitudinal beam;

As shown in FIG. 1, FIG. 2, and FIG. 5, the observation mechanism 4 comprises a micro projector 19 arranged on the bottom surface of the cover plate and a first camera 17, and a second camera 18 symmetrically arranged on both sides of the micro projector 19; wherein, the micro projector 19, the first high-precision digital camera 17 and the second high-precision digital camera 18 are spaced on the same straight line along the axial direction of the horizontal longitudinal beam, and the lenses of the first high-precision digital camera 17 and the second high-precision digital camera 18 are arranged towards the micro projector 19 in an inclined way of 45°; wherein, the micro projector 19 is used to project a number of points to the top surface of the rock sample 8 The first high-precision digital camera 17 and the second high-precision digital camera 18 are used to collect the top photos of the rock sample 8 with digital images, specifically the three-dimensional morphology of the indentation (groove) on the rock surface, so as to draw the three-dimensional image of the rock surface in the computer;

As shown in FIG. 1, the multi-scale penetration mechanism 3 comprises a rotary cutting penetration device at the front side, an indentation detection device at the rear side, and a displacement measurement system arranged between the rotary cutting penetration device and the indentation detection device; wherein, the indentation detection device is used to test the micro scale of rock sample 8 at first, the rotary cutting penetration device is used to test the macro scale of rock sample 8 again, and the displacement measurement system is used to test the dynamic signal of displacement changing with time during drilling and indentation of bit or indenter;

Wherein, the rotary cutting penetration device comprises a first rigid servo motor, a first ball screw, a feed force sensor and a standard twist drill which are connected from top to bottom in turn, and a displacement measurement system arranged between the rotary cutting penetration device and the indentation detection device; the standard twist bit is equipped with various diameter bits, including 0.5 mm diameter standard twist bit, 1 mm diameter standard twist bit, 2 mm diameter standard twist bit and 10 mm diameter standard twist bit; a power amplifier is set between the rigid servo motor and the ball screw to provide the required drilling conditions for the bit; the working principle is as follows: The rigid servo motor drives the ball screw and loads the bit through the power amplifier to realize the rotary cutting of the top surface of rock sample 8; at the same time, the feed force sensor is used to measure the axial WOB of the bit in real time, so as to realize the high precision loading of the bit; the torque sensor is connected with the drill bit through the anti-drying shielded cable, the two sensors can obtain the dynamic signals of the feed force F measured by the feed force sensor and the torque T measured by the torque sensor, which change with time, for subsequent data analysis;

Wherein, the indentation detection device includes a second rigid servo motor, a second ball screw, a vertical rigid spindle and a triangular shell type indenter connected from top to bottom in turn; the triangular shell type indenter is equipped with replaceable indenters of various diameters, including the triangular indenter with side length of 0.5 mm, the triangular indenter with side length of 1 mm and the triangular indenter with side length of 2 mm; each triangular indenter is made of tungsten carbide; the second rigid servo motor is connected with the second driving ball screw through a power amplifier to realize the second rigid servo motor; the working principle of the indentation detection device is as follows: the vertical rigid spindle is driven by the motor to transmit the pressure to the triangular bayonet indenter, which makes indentation on the rock surface under the set load, and uses the displacement measurement system to measure the indentation depth in real time, so as to obtain each size triangle Load displacement curve of indenter;

As shown in FIG. 1, the grinding mechanism 2 comprises a grinding wheel and a drying device; wherein the drying device is an annular disc-shaped structure sheathed on the outer side of the grinding wheel, on which a plurality of hot air pipes are arranged along the annular direction, and each hot air pipe is connected with the hot air circulation box through a pipeline, so that the hot air is vertically ejected from the top surface of the rock sample 8 through a plurality of hot air pipes;

As shown in FIG. 1, FIG. 2, and FIG. 3, the rock sample installation mechanism comprises a square steel fixture 10 for fixing the rock sample 8, an ultrasonic sensor exciting device 9 and an ultrasonic sensor receiving device 11 symmetrically arranged on both sides of the square steel fixture; wherein, the twist bit of the rotary cutting penetration device matches the size of the shell type indenter of the indentation detection device, and the size of the second bearing platform 15 meets the setting of the fixed rock sample 8 with the size of 100 mm×100 mm×180 mm; the ultrasonic sensor exciting device 9 and the ultrasonic sensor receiving device 11 respectively contact with the side wall of the rock sample 8, and the contact surface is coated with a layer of Vaseline; the ultrasonic sensor exciting device 9 and the ultrasonic sensor receiving device 11 have the functions of ultra-low receiving noise and high performance pulse control, which can generate the excitation signal and receive the pulse echo signal; in order to meet the test requirements, the ultrasonic sensor excitation device 9 and the ultrasonic sensor receiving device 11 should ensure that the wavelength of the ultrasonic wave emitted and received by them meets the following requirements: the width of the rock sample is more than ten times of the wavelength, so as to meet the physical premise of an approximate infinite body; in addition, a pressure sensor for detecting the pressure on the rock sample is also arranged on the third moving mechanism of the square steel fixture 10;

The industrial computer controls the three-axis precision motion with multiple driving mechanisms of the three-axis precision motion platform, two cameras and projection equipment of the observation mechanism, each servo motor and sensor of the multi-scale penetration mechanism, grinding wheel and drying device of the grinding mechanism, ultrasonic sensor excitation device 9, ultrasonic sensor receiving device 11 and pressure sensor on the rock sample installation mechanism The platform, observation mechanism, multi-scale penetration mechanism, grinding mechanism and rock sample installation mechanism operate normally according to the above operation mode, and receive the real-time data sent back by the corresponding equipment for subsequent technical personnel to process;

When the holographic scanning system of rock geometric mechanical parameters is used, the NI control and testing system 12 can be installed to assist the three-axis precision motion platform 7. The rock sample installation mechanism with rock sample 8 is arranged in the order of observation mechanism 4, indentation detection device of multi-scale penetration mechanism 3, rotary cutting penetration device of multi-scale penetration mechanism 3, observation mechanism 4 and grinding mechanism 4 The grinding mechanism 2 performs in sequence and circulates to realize the step-by-step and layer by layer scanning of rock sample 8.

Embodiment 2

Figure 6:
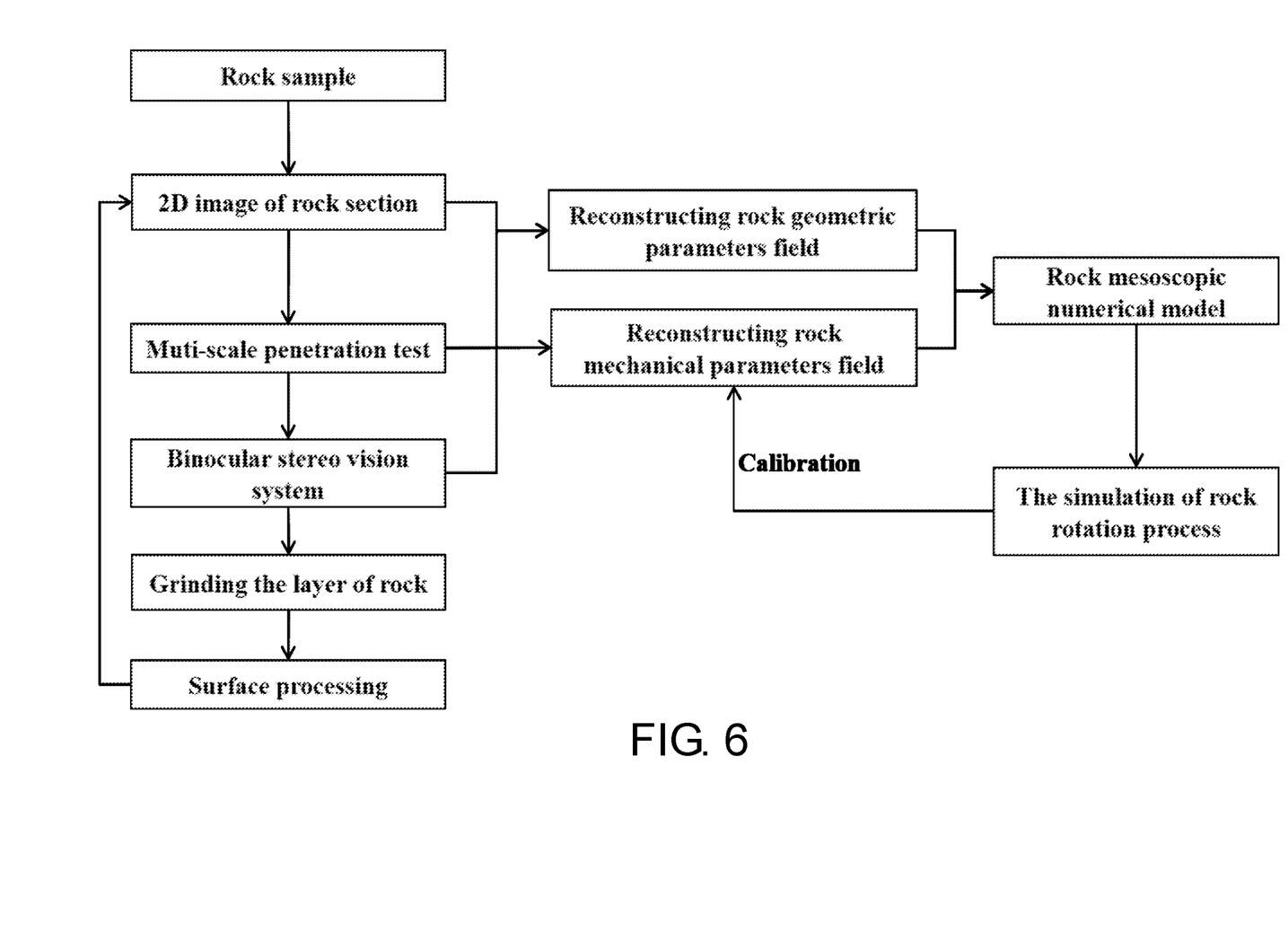
FIG. 6. is a flowchart of rock mechanical-geometric parameters and holographic scanning system.

As shown in FIG. 6, a method for obtaining rock mechanical and geometric parameters by using the holographic scanning system in Embodiment 1, the steps are as follows:

S1. Placing a rock sample 8 taken from the target test rock on the second bearing platform 15, and the bottom of the rock sample 8 is consolidated, and the rock sample is moved to the lower part of the observation mechanism through the three-axis precision motion platform 7; specifically, the rock sample 8 coincides with the central axis of the micro projector 19; then, one of the two cameras symmetrically and obliquely arranged above the rock sample is used the image of the upper surface of the rock sample is captured by a camera;

S2. Dividing the upper surface of the rock sample into 50×50 grids with high resolution by laser, and then using the triangle shell type Berkovich indenter with side length of 0.5 mm for indentation test in each grid according to the preset loading rate $w_1$=10 mm/s (Quasi static state) and indentation depth $L_1$=0.5 mm, so as to obtain the dynamic signal of displacement changing with time $D_1(t)$ by the displacement measurement system during each indentation process and the dynamic signal of load changing with time $F_1(t)$ by the pressure sensor which is sitting at the bottom of the rock sample;

Specifically, because the indenter is not completely rigid, the mechanical parameters of rock can not be obtained directly from the load displacement data; therefore, correlating the elastic modulus of rock sample and indenter by the reduction of elastic modulus $E_r$, and the formula for calculating indentation hardness $H_I$ from indentation test is:

$$H_I = \frac{P_{max}}{A_c},$$

wherein, the formula of reduction of elastic modulus $E_r$ is:

$$E_r = \frac{\sqrt{\pi}}{2} \frac{S}{\sqrt{A_C}},$$

wherein, the formula of elastic modulus $E_i$ is:

$$E_i = (1-v_i^2)\left(\frac{1}{E_r} - \frac{1-v_s^2}{E_s}\right)^{-1},$$

wherein, $P_{max}$ is the maximum indentation force; $E_s$ is the elastic modulus of indenter; $v_s$ is the Poisson's ratio of indenter; $u_i$ is the Poisson's ratio of rock sample;

wherein, $A_c$ is the projected area of indenter:

$$A_C = 24.5 h_C^2,$$

wherein, $h_c$ is the pressure depth, which is obtained by the following formula:

$$h_C = L - \frac{3P_{max}}{4S},$$

Wherein, S is the unloading stiffness, which is obtained from the load-displacement curves at the unloading stage, and the tangent slope at one third of the curve is taken as the unloading stiffness;

And then, obtaining three-dimensional mechanical parameter lattice of the corresponding rock sample including elastic modulus E and Poisson's ratio $\mu_i$ by processing the above parameters;

S3. Acquiring a pulse echo signal of the rock sample by the ultrasonic sensor excitation device and ultrasonic sensor receiving device which are symmetrically arranged on both sides of the rock sample, so as to obtain the longitudinal wave velocity $V_p$ and transverse wave velocity $V_s$ of the ultrasonic wave passing through the rock sample and the density ρ of the rock sample, and then calculating the dynamic elastic modulus Ed and dynamic Poisson's ratio $\mu_d$ of the rock sample;

$$E_d = \frac{\rho V_s^2 (3V_p^2 - 4V_s^2)}{V_p^2 - V_s^2}, \quad \mu_d = \frac{V_p^2 - 2V_s^2}{2(V_p^2 - V_s^2)};$$

S4. Moving the rock sample to the same position as step S1 again, and then projecting the structured light coding pattern on the upper surface of the rock sample, so as to collect images of the upper surface of the rock sample by two cameras which are symmetrically and obliquely arranged above the rock sample, and reconstruct the three-dimensional morphology of the upper surface of the rock sample further;

S5. Polishing the surface of the rock sample, and lubricating and cooling by running water until the upper surface of the rock sample returning to a smooth plane;

S6. Repeating steps S1~S5 to grind the rock sample layer by layer and carrying out the same parameter acquisition experiment until the rock sample reaches the last layer of the preset depth, so as to acquire the 3D parameter lattice of the complete rock sample geometry and mechanics from the accumulation of several layers of single-layer rock parameters;

S7. Using IDW spatial interpolation algorithm to process the three-dimensional lattice of mechanical parameters obtained from step S6:

$$R(x) = \sum_{i=0}^{n} \frac{\omega_i(x) u_i}{S},$$

Wherein, $$\omega_i(x) = \frac{1}{\ln(d(x, x_i))}; \quad S = \sum_{j=0}^{N} \omega_j(x);$$

$x_i$ is the $i^{th}$ sample point; x is the unsolved point; $\omega_i(x)$ is the weight of $x_i$; $u_i$ is the value of $i^{th}$ actual sample point; R(x) is the mechanical parameters of rock obtained from different mechanical tests (indentation test, rotary cutting penetration test); $d(x,x_i)$ is the distance between the measured point and unsolved point:

$$d(x,x_i) = \sqrt{(x-x_i)^2 + (y-y_i)^2 + (z-z_i)^2},$$

Wherein, $x_i$, $y_i$, $z_i$ are the coordinates of the ith sample point on the X, Y, and Z axes, respectively;

Obtaining a virtual lattice of mechanical parameters by weighted averages using distances between interpolation points and the sample points as weight, and then obtaining the three-dimensional mechanical parameter fields of the whole rock sample, including compressive strength field, cohesive force field, internal friction angle field, elastic modulus field and Poisson's ratio field.

In the same way, take two rock samples which are the same as those in the present example, and test them in the same step by using a 1 mm side length bayonet indenter and a 2 mm side length bayonet indenter respectively, so as to obtain the geometric mechanical parameters of rock samples under different load conditions. For example, when the size of the indenter is 0.5 mm, 1 mm and 2 mm, the mesh is divided into 50×50, 80×80 and 100×100.

Embodiment 3

A method for obtaining rock mechanical and geometric parameters by using the holographic scanning system in Embodiment 1; wherein the steps are the same except that step S2 is different from embodiment 1.

Specifically, the specific steps of step S2 in this embodiment are:

Dividing the upper surface of the same rock sample into 40×40 grids with low resolution by laser, and then using the twist drill for rotary cutting penetration test in each grid according to a preset drilling rate $w_2$=75 mm/min and drilling depth $L_2$=5 mm, so as to obtain the dynamic signal of feed force P(t) changing with time by the feed force sensor connected with the twist drill during each cutting process, the dynamic signal of torque M(t) changing with time by the torque sensor set at the adjacent side of the twist drill during each cutting process, and the dynamic signal of displacement $D_2$(t) changing with time by the displacement measurement system during each cutting process, Assuming the feed displacement per revolution is proportionate to the bit pressure P and torque M, $$\frac{1}{K_p} = \frac{1}{2} \tau_f R \delta_c \tan\left(\frac{\pi}{2} - \beta\right),$$

$$\frac{1}{K_m} = \frac{1}{2} \tau_f R^2 \delta_c^2,$$

Wherein, $K_p$ is the slope of the feed displacement-bit pressure curve, which is obtained from signals P(t) and $D_2$(t); $K_m$ is the slope of the feed displacement-bit torque curve, which is obtained from M(t) and $D_2$(t); β is the mean friction angle of the bit; $\tau_f$ is the tensile strength of rock sample; R is radius of the bit, and the cutting coefficient is:

$$\delta_c = \frac{\cos\beta}{\sin\phi \cdot \cos(\phi + \beta)},$$

wherein, the mean friction angle of the bit β is:

$$\beta = \frac{\pi}{2} - \arctan\frac{RK_m}{K_p},$$

Wherein, cutting angle is:

$$\phi = 45° - \frac{\beta}{2},$$

Wherein, the friction angle φ is:

$$\varphi = 90° - 2\phi,$$

Wherein, the normal stress σ and tangential stress τ is obtained from:

$$\sigma = \frac{P}{2aR\sec\theta\tan\phi},$$

$$\tau = \frac{P}{2aR\sec\theta},$$

Wherein, θ is the bit angle. According to the Mohr-coulomb criterion, the cohesive of rock sample is obtained as follows:

$$C = \tau - \sigma\tan\varphi = \frac{P}{2aR\sec\theta} - \frac{P}{2aR\sec\theta\tan\phi},$$

wherein, the compressive strength of rock sample is:

$$R_p = \frac{2C\cos\varphi}{1-\sin\varphi},$$

Wherein, according to the energy conservation theory, the total work done by bit is mainly used to convert into internal energy $W_{inter}$, work done by rock cutting $W_{cutting}$, and work done by pressing into rock sample $W_{press}$, and the corresponding formula is:

$$W_{total} = W_{inter} + W_{cutting} + W_{press},$$

Wherein, according to the bit pressure-time curve $P_{(t)}$, the drilling speed v, the bit torque-time curve $M_{(t)}$, and rotation speed of bit ω, the internal energy $W_{inter}$ is:

$$W_{total} = \int_t P_{(t)} \cdot v \cdot dt + \int_t M_{(t)} \cdot \omega \cdot dt,$$

Wherein, the drilling speed is obtained from:

$$V = \frac{L}{t},$$

Wherein, L is the predetermined depth, t is the drilling time;

Wherein, the internal energy $W_{inter}$ is obtained from:

$$W_{inter} = \int\int\int_{\Omega_1} T_1(\Delta T)C_1 dv + \int\int\int_{\Omega_2} T_2(\Delta T)C_2 dv,$$

Wherein, $T_1(\Delta T)$ is the temperature distribution function of drill; $T_2(\Delta T)$ is the temperature distribution function of rock samples; $C_1$ is the specific heat of drill; $C_1$ is the specific heat of rock samples; $\Omega_1$ is the domain size of drill; $\Omega_2$ is the domain size of rock samples; $T_1(\Delta T)$ is the temperature difference of drill before and after drilling; $T_2(\Delta T)$ is the temperature difference of rock samples before and after drilling;

Wherein, the work done by cutting rock samples can be divided into two parts: the work done by the crushing torque, and the work done by friction torque:

$$W_{Cutting} = \int M_{Crush} \cdot \omega dt + \int M_{Friction} \cdot \omega dt,$$

And elastic modulus of rock samples E is obtained from:

$$E = \frac{F_2^2 L}{2\pi R^2 C(W_{total} - W_{inter} - W_{cutting})},$$

And then obtaining the three-dimensional mechanical parameters including elastic modulus E, cohesive force C and internal friction angle φ and compressive strength $R_p$.

In the same way, take another three rock samples which are the same as those in this example, and test them in the same steps by using the twist drill bit with a diameter of 1 mm, the twist drill bit with a diameter of 2 mm and the twist drill bit with a diameter of 10 mm respectively, so as to obtain the geometric mechanical parameters of rock samples under different WOB conditions. For example, when the diameter of the twist drill is 0.5 mm, 1 mm, 2 mm and 10 mm, the mesh can be set as 10×10, 25×25, 35×35 and 50×50.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for obtaining rock mechanical and geometric parameters of rock samples, the steps being as follows:
   S1, acquiring an image of an upper surface of a rock sample by one of two cameras symmetrically and obliquely arranged above the rock sample;
   S2, dividing the upper surface of the rock sample into $N_1 \times N_1$ grids with high resolution by laser, and then using a Berkovich indenter for indentation test in each grid according to a preset loading rate $w_1$ and an indentation depth $L_1$, so as to obtain a dynamic signal of displacement changing with time $D_1(t)$ by a displacement measurement system during each indentation process, and a dynamic signal of load changing with time $F_1(t)$ by a pressure sensor which is sitting at a bottom of the rock sample, and then obtaining a three-dimensional mechanical parameter lattice of a corresponding rock sample including an elastic modulus E and a Poisson's ratio $\mu_1$ by processing obtained parameters;
   and/or, dividing the upper surface of the same rock sample into $N_2 \times N_2$ grids with low resolution by laser, and then using a twist drill for rotary cutting penetration test in each grid according to a preset drilling rate $w_2$ and a drilling depth $L_2$, so as to obtain a dynamic signal of feed force P(t) changing with time by a feed force sensor connected with the twist drill during each cutting process, a dynamic signal of torque M(t) changing with time by a torque sensor set at an adjacent side of the twist drill during each cutting process, and a dynamic signal of displacement $D_2(t)$ changing with time by a displacement measurement system during each cutting process, and then obtaining three-dimensional mechanical parameters including an elastic modulus E, a cohesive force C and an internal friction angle φ and a compressive strength $R_p$;
   S3, acquiring a pulse echo signal of the rock sample by an ultrasonic sensor excitation device and an ultrasonic sensor receiving device which are symmetrically arranged on both sides of the rock sample, so as to obtain a longitudinal wave velocity $V_p$ and a transverse wave velocity $V_s$ of an ultrasonic wave passing through the rock sample and a density ρ of the rock sample, and then calculating a dynamic elastic modulus Ed and a dynamic Poisson's ratio $\mu_d$ of the rock sample;

$$E_d = \frac{\rho V_s^2 (3V_p^2 - 4V_s^2)}{V_p^2 - V_s^2}, \quad \mu_d = \frac{V_p^2 - 2V_s^2}{2(V_p^2 - V_s^2)};$$

S4, moving the rock sample to a position identical to step S1 again, and then projecting a structured light coding pattern on the upper surface of the rock sample, so as to collect images of the upper surface of the rock sample by the two cameras which are symmetrically and obliquely arranged above the rock sample, and reconstruct a three-dimensional morphology of the upper surface of the rock sample further;
   S5, polishing the upper surface of the rock sample, and lubricating and cooling by running water until the upper surface of the rock sample returning to a smooth plane;
   S6, repeating steps S1~S5 to grind the rock sample layer by layer and carrying out identical parameter acquisition experiment until the rock sample reaches a last layer of a preset depth, so as to acquire a geometry of a complete rock sample and a 3D parameter lattice of mechanical parameters from an accumulation of parameters of several layers of single-layer rock;
   S7, using an IDW spatial interpolation algorithm to process the 3D lattice of mechanical parameters obtained from step S6:

$$R(x) = \sum_{i=0}^{n} \frac{\omega_i(x) u_i}{S},$$

wherein, $$\omega_i(x) = \frac{1}{\ln(d(x, x_i))}; S = \sum_{j=0}^{N} \omega_j(x);$$

$x_i$ is an $i^{th}$ sample point; x is an unsolved point; $\omega_i(x)$ is a weight of $x_i$; $u_i$ is an actual value of the $i^{th}$ sample point; R(x) is mechanical parameters of rock obtained from different mechanical tests (indentation test, rotary cutting penetration test); $d(x,x_i)$ is a distance between the sample point and the unsolved point:

$$d(x,x_i)=\sqrt{(x-x_i)^2+(y-y_i)^2+(z-z_i)^2},$$

wherein, $x_i$, $y_i$, $z_i$ are coordinates of the $i^{th}$ sample point on X, Y, and Z axes, respectively;

obtaining a virtual lattice of mechanical parameters by weighted averages using distances between interpolation points and the sample points as weight, and then obtaining three-dimensional mechanical parameter fields of the complete rock sample, including a compressive strength field, a cohesive force field, an internal friction angle field, an elastic modulus field and a Poisson's ratio field.

2. The method for obtaining the geometrical and mechanical parameters of rock samples according to claim 1, wherein when the indentation test is conducted, a value of $N_1$ varies according to a shape of the Berkovich indenters, and ranges from 50×50 to 100×100, and an area of the Berkovich indenter is 1/200~1/50 of an area of the upper surface of the rock sample, and the preset depth is from 0.5 mm to 2 mm with quasi-static loading.

3. The method for obtaining the geometrical and mechanical parameters of rock samples according to claim 1, wherein when the indentation test is conducted, the method to obtain the three-dimensional mechanical parameters is as follows:

correlating the elastic modulus of the rock sample and the Berkovich indenter by a reduction of elastic modulus $E_r$, and a formula for calculating an indentation hardness $H_I$ from the indentation test is:

$$H_I = \frac{P_{max}}{A_c},$$

wherein, a formula of the reduction of elastic modulus $E_r$ is:

$$E_r = \frac{\sqrt{\pi}}{2} \frac{S}{\sqrt{A_C}},$$

wherein, a formula of elastic modulus $E_i$ is:

$$E_i = (1 - v_i^2)\left(\frac{1}{E_r} - \frac{1-v_s^2}{E_s}\right)^{-1},$$

wherein, $P_{max}$ is a maximum indentation force; $E_s$ is an elastic modulus of the Berkovich indenter; $v_s$ is a Poisson's ratio of the indenter; $u_i$ is a Poisson's ratio of the rock sample;

wherein, $A_c$ is a projected area of the Berkovich indenter:

$$A_C=24.5h_C^2,$$

wherein, $h_c$ is a pressure depth, which is obtained by a following formula:

$$h_C = L - \frac{3P_{max}}{4S},$$

wherein, S is an unloading stiffness, which is obtained from a load-displacement curves at an unloading stage, and a tangent slope at one third of a curve is taken as the unloading stiffness.

4. The method for obtaining the geometrical and mechanical parameters of rock samples according to claim 1, wherein when the rotary cutting penetration test is conducted, details of obtaining three-dimensional mechanical parameters of the rock sample are as follows:

assuming a feed displacement per revolution being proportionate to a bit pressure P and a torque M, $$\frac{1}{K_p} = \frac{1}{2}\tau_f R \delta_c \tan\left(\frac{\pi}{2} - \beta\right),$$

$$\frac{1}{K_m} = \frac{1}{2}\tau_f R^2 \delta_c^2,$$

wherein, $K_p$ is a slope of a feed displacement-bit pressure curve, which is obtained from signals P(t) and $D_2(t)$; $K_m$ is a slope of the feed displacement-bit torque curve, which is obtained from M(t) and $D_2(t)$; $\beta$ is a mean friction angle of the bit; $\tau_f$ is the tensile strength of the rock sample; R is a radius of the bit, and a cutting coefficient is:

$$\delta_c = \frac{\cos \beta}{\sin \phi \cdot \cos (\phi + \beta)},$$

wherein, a mean friction angle of the bit $\beta$ is:

$$\beta = \frac{\pi}{2} - \arctan\frac{RK_m}{K_p},$$

wherein, a cutting angle is:

$$\phi = 45° - \frac{\beta}{2},$$

wherein, a friction angle $\varphi$ is:

$$\varphi=90°-2\phi,$$

wherein, a normal stress $\sigma$ and a tangential stress $\tau$ are obtained from:

$$\sigma = \frac{P}{2aR\sec\theta\tan\phi},$$

$$\tau = \frac{P}{2aR\sec\theta},$$

wherein, θ is the bit angle, according to a Mohr-coulomb criterion, the cohesive force of the rock sample is obtained as follows:

$$C = \tau - \sigma \tan\varphi = \frac{P}{2aR\sec\theta} - \frac{P}{2aR\sec\theta\tan\phi},$$

wherein, a compressive strength of the rock sample is:

$$R_p = \frac{2C\cos\varphi}{1-\sin\varphi},$$

wherein, according to an energy conservation theory, a total work done by the bit is mainly used to convert into an internal energy $W_{inter}$, a work done by rock cutting $W_{cutting}$, and a work done by pressing into rock sample $W_{press}$, and a corresponding formula is:

$$W_{total} = W_{inter} + W_{cutting} + W_{press},$$

wherein, according to a bit pressure-time curve $P_{(t)}$, a drilling speed v, a bit torque-time curve $M_{(t)}$, and a rotation speed of the bit ω, the internal energy $W_{inter}$ is:

$$W_{total} = \int_t P_{(t)} \cdot v \cdot dt + \int_t M_{(t)} \cdot \omega \cdot dt,$$

wherein, the drilling speed is obtained from:

$$V = \frac{L}{t},$$

wherein, L is a predetermined depth, t is a drilling time; wherein, the internal energy $W_{inter}$ is obtained from:

$$W_{inter} = \iiint_{\Omega_1} T_1(\Delta T) C_1 dv + \iiint_{\Omega_2} T_2(\Delta T) C_2 dv,$$

wherein, $T_1(\Delta T)$ is a temperature distribution function of the twist drill; $T_2(\Delta T)$ is a temperature distribution function of the rock sample; $C_1$ is a specific heat of the twist drill; $C_1$ is a specific heat of the rock sample; $\Omega_1$ is a domain size of the twist drill; $\Omega_2$ is a domain size of the rock sample; $T_1(\Delta T)$ is a temperature difference of the twist drill before and after drilling; $T_2(\Delta T)$ is a temperature difference of the rock sample before and after drilling;

wherein, the work done by cutting the rock sample is divided into two parts: a work done by a crushing torque, and a work done by a friction torque:

$$W_{Cutting} = \int M_{Crush} \cdot \omega dt + \int M_{Friction} \cdot \omega dt,$$

and the elastic modulus of the rock sample E is obtained from:

$$E = \frac{F_2^2 L}{2\pi R^2 C (W_{total} - W_{inter} - W_{cutting})}.$$

5. The method for obtaining the geometrical and mechanical parameters of rock samples according to claim 1, wherein when the indentation test is conducted, the value of $N_2$ varies according to a shape of drill bits, and ranges from 10×10 to 50×50, and a diameter of the twist drill is 1/50 to 1/10 of an area of the upper surface of the rock sample, and the drilling depth L2 is from 0.5 mm to 2 mm.

6. The method for obtaining the geometrical and mechanical parameters of rock samples according to claim 1, wherein in step S3, a wavelength emitted by the ultrasonic sensor excitation device is one tenth of a path length through the rock sample.

7. A holographic scanning system for realizing the method for obtaining the geometrical and mechanical parameters of rock samples according to claim 6, wherein an equipment includes an observation mechanism arranged on a three-axis precision motion platform, a multi-scale penetration mechanism, a grinding mechanism, a rock sample installation mechanism, and an industrial computer for controlling an operation of the three-axis precision motion platform, the observation mechanism, the multi-scale penetration mechanism, the grinding mechanism and the rock sample installation mechanism; wherein, the three-axis precision motion platform comprises a first motion mechanism which is configured to realize up and down motion, a second motion mechanism which is arranged on the first motion mechanism and is configured to realize left and right motion, a third motion mechanism which is arranged on the second motion mechanism and is configured to realize back and forth motion, and a cover plate which is located above the three motion mechanisms; wherein the observation mechanism, the multi-scale penetration mechanism, and the grinding mechanism are successively installed on a floor of the cover plate, and the rock sample installation mechanism is installed on the third moving mechanism;

the observation mechanism comprises a micro projector arranged on a bottom surface of the cover plate and a first camera, and a second camera symmetrically arranged on both sides of the micro projector; wherein a lens of the first camera and a lens of the second camera are arranged in an oblique manner towards the micro projector;

the multi-scale penetration mechanism comprises a rotary cutting penetration device at a front side, an indentation detection device at a rear side, and a displacement measurement system arranged between the rotary cutting penetration device and the indentation detection device; wherein, the rotary cutting penetration device comprises a first rigid servo motor, a first ball screw, a feed force sensor and a standard twist drill which are connected from top to bottom in turn, and a displacement measurement system arranged between the rotary cutting penetration device and the indentation detection device, the indentation detection device includes a second rigid servo motor, a second ball screw, a vertical rigid spindle and a triangular shell type indenter connected from top to bottom in turn;

the rock sample installation mechanism comprises a square steel fixture for fixing the rock sample, an ultrasonic sensor exciting device and an ultrasonic sensor receiving device symmetrically arranged on both sides of the square steel fixture; a pressure sensor for detecting a pressure on the rock sample is also arranged on the third moving mechanism of the square steel fixture.

8. The holographic scanning system according to claim 7, wherein the grinding mechanism comprises a grinding wheel and a drying device; wherein the drying device is an annular disc-shaped structure sheathed on an outer side of the grinding wheel, on which a plurality of hot air pipes are arranged along a annular direction, and each hot air pipe is connected with a hot air circulation box through a pipeline, so that a hot air is vertically ejected from the upper surface of the rock sample through a plurality of hot air pipes.

* * * * *